US005763425A

United States Patent [19]
Keimowitz et al.

[11] Patent Number: 5,763,425
[45] Date of Patent: *Jun. 9, 1998

[54] SUPPRESSION OF THROMBOXANE LEVELS BY PERCUTANEOUS ADMINISTRATION OF ASPIRIN

[75] Inventors: Rudolph M. Keimowitz, La Crosse, Wis.; Desmond J. Fitzgerald, Dublin, Ireland

[73] Assignee: Gundersen Clinic, Ltd., La Crosse, Wis.

[*] Notice: The term of this patent shall not extend beyond the expiration date of Pat. No. 5,240,917.

[21] Appl. No.: 780,426

[22] Filed: Jan. 8, 1997

Related U.S. Application Data

[63] Continuation of Ser. No. 339,646, Nov. 14, 1994, abandoned, which is a continuation of Ser. No. 47,516, filed as PCT/US92/02576, Apr. 2, 1992, abandoned, which is a division of Ser. No. 899,209, Jun. 16, 1992, Pat. No. 5,240,917, which is a continuation-in-part of Ser. No. 680,195, Apr. 3, 1991, abandoned.

[51] Int. Cl.⁶ .................... A61K 31/60; A61K 9/70
[52] U.S. Cl. .................... 514/165; 424/449; 514/947
[58] Field of Search .................... 514/165, 947; 424/449

[56] References Cited

U.S. PATENT DOCUMENTS

| | | |
|---|---|---|
| 3,598,122 | 8/1971 | Zaffereal . |
| 4,012,508 | 3/1977 | Burton . |
| 4,219,548 | 8/1980 | Reller . |
| 4,228,162 | 10/1980 | Luzzi et al. . |
| 4,286,592 | 9/1981 | Chandrasekaran . |
| 4,460,368 | 7/1984 | Allison et al. . |
| 4,476,115 | 10/1984 | Reed .................... 424/164 |
| 4,640,689 | 2/1987 | Sibalis . |
| 4,654,209 | 3/1987 | Leslie et al. .................... 424/80 |
| 4,665,063 | 5/1987 | Bar-Shalom . |
| 4,810,699 | 3/1989 | Sabatucci et al. . |
| 4,948,588 | 8/1990 | Kamiya et al. .................... 424/436 |
| 4,954,487 | 9/1990 | Cooper et al. .................... 514/159 |
| 4,970,081 | 11/1990 | Frisbee .................... 424/480 |
| 4,975,269 | 12/1990 | Chavkin et al. . |
| 5,093,133 | 3/1992 | Wisniewski et al. . |
| 5,120,716 | 6/1992 | Miyazawa et al. .................... 514/23 |
| 5,223,267 | 6/1993 | Nichols .................... 424/489 |
| 5,240,917 | 8/1993 | Keimowitz et al. . |
| 5,254,346 | 10/1993 | Tucker et al. .................... 424/449 |

FOREIGN PATENT DOCUMENTS

| | | |
|---|---|---|
| 0 055 635 | 7/1982 | European Pat. Off. . |
| 0 162 239 | 11/1985 | European Pat. Off. . |
| 2 295 753 | 7/1976 | France . |
| 34 13 052 | 12/1984 | Germany . |
| WO 91/00096 | 1/1991 | WIPO . |
| WO 93/12799 | 7/1993 | WIPO . |
| WO 95/08330 | 3/1995 | WIPO . |

OTHER PUBLICATIONS

Chem Abst. 98 (1983)—46600x, Bertele et al.
Chem Abst. 108 (1988)—180111s, Arai.
Chem Abst. 110 (1989)—141529f, McKie et al.
Chem Abst. 111 (1989)—89965Z, Danesh et al.
Chest, vol. 95, No. 2, Feb. 1989, J. Hirsh et al.: *Aspirin and other platelet active drugs—Relationship among dose, effectiveness, and side effects*, pp. 12S–18S.
Japanese Pharmacology & Therapeutics, Yakuri to Chiryo, vol. 16, No. 1, Jan. 1988, S.–I. Naito et al.: *Percutaneous absorption of salicylic acid derivatives*, pp. 17–25.
J.E.F. Reynolds et al.: *Martindale the Extra Pharmacopoeia*, 29th Ed., 1989, pp. 3–8, The Pharmaceutical Press, London GB.
The Journal of Burn Care & Rehabilitation, vol. 6, No. 6, Nov./Dec. 1985, J.P. Heggers et al.: *Thromboxane inhibitors for the prevention of progressive dermal ischemia due to the thermal injury*, pp. 466–468.
The Journal of Clinical Investigation, vol. 69, No. 6, Jun. 1982, P. Patrignani et al.: *Selective Cumulative Inhibition of Platelet Thromboxane Production by Low–dose Aspirin in Healthy Subjects*, pp. 1366–1372.
New England Journal of Medicine, vol. 325, 1991, Thun et al.: *Aspirin Use and Reduced Risk of Fatal Colon Cancer*, pp. 1593–1596.
Van Moorleghem G L, Derwent WPI, Derwent Publications, Ltd., Week 7647, WPI Acc No: 76–87300X (Abstract of French Patent Application No. 2,297,612, Sep. 17, 1976).
Teisan Seiyaku, Derwent WPI, Derwent Publications, Ltd., Week 8636, WPI Acc No: 86–236772 (Abstract of Japanese Patent Application No. 61–167615, Jul. 29, 1986).
Teikoku Seiyaku, Derwent WPI, Derwent Publications, Ltd., Week 8939, WPI Acc No: 89–280859 (Abstract of Japanese Patent Application No. 1–203336, Aug. 16, 1989).
Nikko Chemicals, Derwent WPI, Derwent Publications, Ltd., Week 8945, WPI Acc No: 89–327620 (Abstract of Japanese Patent Application No. 1–242521, Sep. 27, 1989).
Kyowa Hakko Kogyo, Derwent WPI, Derwent Publications, Ltd., Week 9125, WPI Acc No: 91–183201 (Abstract of Japanese Patent Application No. 3–112926, May 14, 1991).

*Primary Examiner*—William R. A. Jarvis
*Attorney, Agent, or Firm*—McDonnell Boehnen Hulbert & Berghoff

[57] ABSTRACT

A method is disclosed for inducing thromboxane suppression in a mammalian subject by percutaneously administering a pharmaceutical composition containing aspirin. Articles useful for practicing the therapeutic methods of the invention are also disclosed.

7 Claims, 3 Drawing Sheets

SUPPRESSION OF THROMBOXANE LEVELS BY PERCUTANEOUS ADMINISTRATION OF ASPIRIN

This application is a Continuation of application Ser. No. 08/339,646, filed Nov. 14, 1994, now abandoned, which is a continuation of Ser. No. 08/047,516, filed Apr. 19, 1993, now abandoned, which is divisional of Ser. No. 07/899,209, filed Jun. 16, 1992, now U.S. Pat. No. 5,240,917, which is a continuation-in-part of Ser. No. 07/680,195, filed Apr. 3, 1991, now abandoned. This application also claims priority from International Application No. PCT/US92/02576, filed Apr. 2, 1992.

FIELD OF THE INVENTION

The present invention relates to the use of acetyl salicylic acid (aspirin) as an antithrombotic agent and as an agent to treat other medical conditions benefiting from suppression of thromboxane levels. Particularly, the present invention relates to the percutaneous administration of aspirin for inducing such effects and treating such conditions.

BACKGROUND OF THE INVENTION

With the recognition of the role of antithrombotic agents in clinical medicine, investigators have pursued their efficacy, optimal dose, route of administration and safety. Aspirin has been found to be an effective antithrombotic agent in patients with cerebrovascular disease and ischemic heart disease. Aspirin may also have other antithrombotic applications. Although aspirin has become widely used as an antithrombotic agent, it still exhibits undesirable side effects, including gastrointestinal toxicity which is probably dose related.

To induce its suppressive effects, aspirin irreversibly acetylates the enzyme cyclo-oxygenase found in platelets and vascular wall cells [Burch et al., J. Clin. Invest. 61:314 (1978); Majerus, J. Clin. Invest. 72:1521 (1983); Roth et al., J. Clin. Invest. 56:624 (1975)]. Cyclo-oxygenase converts arachidonic acid to thromboxane-$A_2$ ($TXA_2$) in platelets and to prostaglandin-$I_2$ ($PGI_2$ or prostacyclin) in vascular walls [see for example, FitzGerald et al., J. Clin. Invest. 71:676 (1983); Preston et al., N. Engl. J. Med. 304:76 (1981)]. $TXA_2$ induces platelet aggregation and vasoconstriction, while $PGI_2$ inhibits platelet aggregation and induces vasodilation. In other words, aspirin can have both an antithrombotic effect (by reducing $TXA_2$ production) and a thrombogenic effect (by reducing $PGI_2$ production). As a result, striking an appropriate balance between aspirin's effects on $TXA_2$ and $PGI_2$ production has been a goal of aspirin therapy under these circumstances.

It is generally accepted that when aspirin is administered in doses of approximately 1,000 mg/day, it inhibits both $TXA_2$ and $PGI_2$ synthesis [Weksler et al., N. Engl. J. Med. 308:800 (1983)]. Daily administration of very low doses of aspirin (approximately 40 mg/day) has been reported to inhibit thromboxane-$B_2$ synthesis in vitro and to reduce the urinary excretion of 2,3-dinor-thromboxane-$B_2$ (both of which are metabolites of $TXA_2$), without producing significant changes in the urinary excretion of 6-keto-prostaglandin-$F_1$a and 2,3-dinor-6-keto-prostaglandin-$F_1$a (which are both metabolites of $PGI_2$ production) [Patrignani et al., J. Clin. Invest. 69–1366 (1982); FitzGerald et al., supra]. While 40 mg/day has no significant effect on prostacyclin biosynthesis, it does have some measurable effect [FitzGerald et al., supra]. Moreover this dose does not suppress 2,3-dinor-$TXB_2$ very well and it is not known whether it suppresses bradykinin-stimulated prostacyclin formation. Therefore, this dose has not been demonstrated to provide selective inhibition of thromboxane synthesis without also inhibiting prostacyclin formation.

In contrast, others have reported that equally low doses of aspirin reduced $PGI_2$ synthesis by 50% in both arterial and venous tissue [Preston et al., supra], and even lower doses (20 mg/day for 1 week) have been reported to inhibit $PGI_2$ synthesis in both arterial and venous tissue by 50% in atherosclerotic patients [Weksler et al., supra]. It has been proposed that although this differential effect on the inhibition of $TXA_2$ and $PGI_2$ synthesis has been reported when urinary metabolites are measured to assess inhibition, there is no significant evidence for this differential effect when $PGI_2$ synthesis is measured by assay of vascular wall biopsy tissue or when the assays for $TXA_2$ and $PGI_2$ are performed on blood samples [Weksler et al., supra]. However, it is not possible to achieve platelet selectivity with standard oral aspirin. Inhibition of basal $PGI_2$ biosynthesis is similar over doses of 80–2,400 mg/day and bradykinin-stimulated $PGI_2$ formation is abolished on oral aspirin 75 mg/day.

Aspirin has also been found to be an effective treatment for other medical conditions which benefit from lowering of $TXA_2$ levels. For example, it has been reported that daily doses of aspirin given during the third trimester of pregnancy can significantly reduce the incidence of pregnancy-induced hypertension and preeclamptic toxemia in women at high risk for these disorders as a result of reductions in $TXA_2$ levels [Schiff et al., N. Engl. J. Med. 321:351 (1989)]. Aspirin has also been reported to provide positive effects in women at risk for pregnancy-induced hypertension. Low doses of aspirin were reported to selectively suppress maternal thromboxane levels, but only partially suppressed neonatal thromboxane, allowing hemostatic competence in the fetus and newborn [Benigni et al., N. Engl. J. Med. 321:357 (1989)]. The use of aspirin for reducing the risk of fatal colon cancer has also been proposed [Thun et al., N. Engl. J. Med. 325:1593 (1991)]. Reduction of thromboxane levels has also been suggested as a means for treating thrombosis in patients having antiphospholipid syndrome associated with lupus [Lellouche et al., Blood 78:2894 (1991)]. Low-dose aspirin has also been suggested as therapy for migraine headache [see for example, Buring et al., JAMA 264(13) (1990)]. The role of arachidonic acid metabolites (e.g., $TXA_2$ and $PGI_2$) in migraine have also been invesitaged [see for example, Parantainen et al., "Prostaglandins in the Pathophysiology of Migraine" in P. B. Curtis—Prior (ed.), *Prostaglandins: Biology and Chemistry of Prostaglandins and Related Eicosanoids* (New York: Churchill Livingstone 1988), pp. 386–401; Puig-Parellada et al., Headache 31(3) :156 (1991); Tuca et al., Headache 29(8):498 (1989); Nattero et al, Headache 29(4):233 (1989)].

The use of aspirin as a thromboxane suppressant has been hampered by its tendency to cause gastric bleeding upon traditional administration of aspirin in oral dose form Studies have reported that aspirin produces erythema of the gastric mucosa in approximately 80% of patients with rheumatic diseases, gastric erosions in approximately 40%, and gastric ulcer in 15% [Silvoso et al., Ann. Intern. Med. 91:517 (1979)]. Aspirin applied topically to gastrointestinal tissue damages gastric mucosa and induces occult gastrointestinal bleeding [Croft et al., Br. Med. J. 1:137 (1967)]. Intravenous administration of aspirin may also produce some effects on gastric mucosa which is less pronounced with parenteral than with oral administration [Grossman et al., 40:383 (1961)]. Oral administration of diluted solutions of aspirin cause considerably less bleeding than similar doses in tablet form, and aspirin solutions containing antacids with sufficient buffering capacity cause no measurable blood loss [Leonards et al., Arch. Intern. Med. 129:457 (1972)]. Enteric-coated aspirin use results in less gastric and duodenal mucosal injury than regular aspirin [Graham et al., Ann. Intern. Med. 104:390 (1986)].

It would, therefore, be desirable to provide an appropriate dosage form of aspirin which will provide thromboxane suppressing effects, preferably selective thromboxane suppressing effects, and will also avoid the adverse side effects observed with aspirin dosage forms currently employed in aspirin therapies.

Several reports have been made of the incorporation of aspirin into a various analgesic preparations. U.S. Pat. No. 4,948,588 discloses the use of ether derivatives of glycerols or polyglycerols as percutaneous absorption accelerators. Analgesics, such as morphine, codeine and aspirin, are suggested as possible active agents for use with these accelerators. An example discloses incorporation of aspirin into a suppository which was administered to male rabbits.

U.S. Pat. No. 4,654,209 discloses creams containing nitroglycerine and other active ingredients. Analgesics, such as aspirin, are suggested as active ingredients. An example makes a cream containing 5–15% aspirin by weight which was applied to the skin of the abdomen, thigh or back of subjects, resulting in positive blood and urine tests for the active ingredient.

U.S. Pat. No. 4,476,115 discloses analgesic compositions applied to skin together with or subsequent to the application of a non-toxic water-soluble sulfite compound. Examples described the preparation of mixtures of aspirin and anhydrous sodium sulfite which was applied to the skin of a mammal and covered with a water impervious plastic sheet held in place by adhesive tape. Bioavailability was observed within 30 to 40 minutes as evidence by increased mobility of the subject and reduction of stiffness.

Although such aspirin preparations have been used for their analgesic effects, such preparations have not to applicant's knowledge been applied for therapy in which thromboxane suppression is desired.

SUMMARY OF THE INVENTION

In accordance with the present invention, thromboxane suppressing effects are provided without the gastric side effects normally associated with aspirin therapy. Aspirin is applied topically to a patient's skin such that it is percutaneously absorbed. The aspirin is taken into the bloodstream in quantities sufficient to inhibit $TXA_2$ synthesis. The methods of the present invention can be used to treat any medical condition for which suppression of thromboxane levels is beneficial. For example, such methods can be used to produce antithrombotic effects and to treat pregnancy-induced hypertension and preeclamptic toxemia.

The aspirin can be applied by use of a support or carrier which contains the aspirin preparation, including without limitation suspensions, creams, solutions, patches (adhesive and non-adhesive), gels, ointments, plasters, plaques or other known forms for applying topical agents, as long as the aspirin can be delivered in a form which will penetrate the skin (such as, for example, in a solubilized form). Articles can be made which incorporate the aspirin preparation, in some instances with a support or carrier (such as in the form of an adhesive patch), which are useful in practicing the therapeutic methods of the present invention.

Absorption enhancing agents and other pharmaceutical carriers can be incorporated into the aspirin preparation in accordance with known methods. Propylene glycol, with or without isopropyl or ethyl alcohol, is a preferred carrier. In addition to aspirin, other active ingredients can be incorporated into preparations for use in the present invention such as anti-arrythmics, blood pressure regulators, etc.

The aspirin content of the preparation will vary depending on the form of administration used. In one embodiment, the aspirin is applied at 750 mg/day at a concentration of about 9% aspirin. To achieve the desired suppression effects, aspirin is preferably administered over a period of several days until $TXA_2$ levels are reduced to minimal levels, preferably less than 50% of baseline levels, more preferably less than 10% of baseline levels, most preferably less than 5% of baseline levels. Although $TXA_2$ levels will be reduced almost immediately, substantial reductions in those levels are achieved and maintained by daily administration over a course of several days, preferably at least 4 days, most preferably at least 10 days.

Any form of aspirin may be employed in practicing the present invention as long as the active compound can penetrate the skin. The term "aspirin" as used herein and the appended claims is intended to encompass, without limitation, all such forms. Suitable forms may include acetyl salicylate and salts, esters, hydrates, etc. thereof. Particular salts which may be used include without limitation the lactate, sodium and lysine salts of aspirin Compositions and articles of manufacture of the present invention may also include aspirin in a first form (such as for example, an aspririn "prodrug" or another stabilized compound containing acetyl salicylate) which is later converted to a second form which can penetrate the skin.

In studying the effects of the methods of the present invention platelet cyclooxygenase activity was used as a measure of aspirin bioavailability, in addition to plasma drug levels. A preferred vehicle, propylene glycol and ethanol, is widely used as a skin permeant and was chosen to avoid ex vivo deacetylation to the inactive metabolite, salicylate. In certain preferred embodiments, aspirin applied daily induced a dose-dependent inhibition of platelet cyclooxygenase, as measured by serum $TXB_2$. Maximum inhibition was achieved at 10 days and exceeded 95% at the highest dose. Such a degree of suppression is preferred to sufficiently inhibit platelet function and $TXA_2$ biosynthesis in vivo. Inhibition of urinary TX-M followed a similar pattern. TX-M is a major enzymatic metabolite of $TXB_2$ and its excretion is an index of $TXA_2$ biosynthesis in vivo. In contrast, the vehicle alone had no effect on serum $TXB_2$ or urinary TX-M. Following withdrawal of therapy, serum $TXB_2$ and TX-M recovered gradually over a period of days. This is consistent with inhibition of platelet cyclooxygenase in vivo. As the enzyme is inhibited irreversibly, recovery of platelet $TXA_2$ biosynthesis parallels the formation of new platelets, a process that has a half-life of 5 days.

In contrast to the marked inhibition of $TXA_2$, there was little inhibition of basal or stimulated $PGI_2$ formation. Basal PGI-M excretion, an index of in vivo $PGI_2$ biosynthesis, decreased 24% by day 4 on the highest dose of dermal aspirin. No further inhibition occurred despite continued application and by day 10, PGI-M excretion remained at 83% of baseline. This may reflect the contribution of platelet endoperoxides to $PGI_2$ biosynthesis or local inhibition of $PGI_2$ biosynthesis. $PGI_2$ formation in response to bradykinin infusion was also unaltered. In contrast, oral aspirin 75 mg/day suppressed basal and bradykinin-stimulated PGI-M excretion, as previously demonstrated.

The preservation of vascular cyclooxygenase is consistent with the low bioavailability of the dermal aspirin. Plasma aspirin and salicylate were determined using a highly sensitive assay that can measure levels of <0.1 ng/ml. Following oral aspirin 325 mg or 162.5 mg, peak plasma aspirin levels were 2.0 and 1.3 ug/ml, respectively. In contrast, following dermal aspirin, plasma levels peaked at 237±114 ng/ml and plasma salicylate peaked at 788±114 ng/ml.

These data suggest that aspirin applied to the skin is absorbed very slowly, resulting in a delaying a delayed onset and offset of activity. Platelets passing through the site of application are inhibited by relatively high concentrations of aspirin. A similar localized platelet effect has been reported with oral aspirin, where inhibition of serum $TXB_2$ occurs prior to the appearance of aspirin systematically. As platelet cyclooxygenase cannot recover, cumulative inhibition of all platelets occurs over time. In contrast, little aspirin reaches the systemic circulation, so that vascular cyclooxygenase is protected. The poor systemic bioavailability of dermal aspirin presumably reflects low skin permeability and dilution and inactivation in the venous and pulmonary circulations.

Although in one subject there were no histological changes following 10 days of drug application at 250 mg/day, skin reactions were noted in 30% of the subjects, including erythema and peeling. Similar reactions occur with high concentrations of salicylate. Preliminary studies show that reactions may be avoided by alternate day application. Such regimens have been used without reactions for up to 8 weeks. Alternatively, modifications to the preparation, such as using the lactate or sodium salt of aspirin, or the vehicle, may be better tolerated. Lower concentrations and smaller doses may be feasible under occlusive conditions, which enhance drug absorption.

When the methods of the present invention are used, as demonstrated further below with respect to certain preferred embodiments, aspirin is absorbed through the skin and results in marked and selective inhibition of platelet cyclooxygenase. This approach may prove useful in patients with known peptic ulcer disease or during coincident administration of anticoagulants, such as Warfarin or heparin. The methods of the present invention should be particularly helpful in co-administration with warfarin as the high incidence of bleeding associated with oral aspirin and Warfarin is gastrointestinal and thought to be secondary to the oral aspirin effect.

Use of such aspirin preparations in accordance with the present invention provides thromboxane suppression effects, preferably selective suppression effects, without exposing the gut to high local concentrations of aspirin, which should permit its use in patients with, for example, gastric intolerance, or duodenal or gastric ulcers.

DETAILED DESCRIPTION OF PREFERRED EMBODIMENTS

The advantages of the present invention can be appreciated by reference to the following example which is meant to illustrate, but not limit, the present invention.

EXAMPLE 1

Five healthy adult volunteers (3 male, 2 female) were studied. Each refrained from ingesting oral aspirin for two weeks prior to study. Prior to treatment in accordance with the present invention, baseline thromboxane levels and hemoccults were obtained.

Thromboxane levels were measured by assaying for blood levels of thromboxane-$B_2$ in accordance with the method described in Braden et al., Circulation 82:178 (1990). Thromboxane levels can also be measured in either blood or urine according to known methods which include those without limitation disclosed in the following references: Hirsh et al., supra; Robertson et al., N. Engl. J. Med. 304:998 (1981); Pedersen et al., N. Engl. J. Med. 311:1206 (1984); Patrignani et al., J. Clin. Invest. 69:1366 (1982); Preston et al., 304:76 (1981); Hirsh et al., N. Engl. J. Med. 304:685 (1981).

Salicylate levels were determined according to the following method. The procedure for determining salicylate is based on the formulation of a violet colored complex between ferric iron and phenols. Substances other than salicylate may react to give a positive test, but false negative results do not occur. The color reagent contains acid and mercuric ions to precipitate protein. References relevant to the assay method include: Trinder, Biochemical Journal 57:301 (1954); Tietz, Fundamentals of Clinical Chemistry, W. B. Saunders Co., 1970, pp. 882–884; Meites, Pediatric Clinical Chemistry, A.A.C.C., 1977, p. 192.

Trinder's Reagent was prepared as follows. 40 gm of mercuric chloride was dissolved in about 700 ml of deionized water by heating. The solution was cooled and 120 ml of 1N HCl and 40 gm of ferric nitrate, $Fe(NO_3)_3 9H_2O$, were added. When all the ferric nitrate had dissolved, the solution was diluted to a total volume of 1000 ml with deionized water. This stock solution is stable for approximately one year.

Standards were prepared as follows. A Stock Standard (200 mg/100 ml) was prepared by dissolving 464 mg of sodium salicylate in deionized water and diluted to a total volume of 200 ml. A few drops of chloroform were added as a preservative. This standard solution is stable for approximately 6 months under refrigeration. 5, 10, 25, and 40 ml of stock standard were pipetted into a series of 100 ml volumetric flasks, diluted to a total of 100 ml with deionized water, and mixed.

0.2 ml of serum or heparinized plasma were used as sample specimens. 0.2 ml of each standard and each sample was pipetted into respectively labeled disposable polystyrene tubes. Into another polystyrene tube, 0.2 ml of deionized water was pipetted to be used as a reagent blank. 1.0 ml of deionized water was added to all tubes. 1.0 ml of Trinder's reagent was then added to all tubes, which were mixed and let stand tubes for 5 minutes. The tubes were then centrifuged for 10 minutes. The clear supernatant (minimum of 1.0 ml) wa placed into respectively labeled 10×75 nm cuvettes. Samples were analyzed by reading % T at 540 nm against the reagent blank set at 100% T. Sample values were compared with standard values to determine levels. Results over 75 mg percent were diluted and re-analyzed.

A preparation of aspirin in isopropyl alcohol and propylene glycol was prepared by mixing "Aspirsol"™ topical aspirin (NDC 54102-001-01; commercially available from TERRI Pharmaceuticals, Inc., PO Box 6454, Kingwood, Tex. 77325) in accordance with the package instructions except that 8 ml instead of 10 ml of the suspending solution was used. The resulting solution contained approximately 9% aspirin rather than the 7-8% indicated on the package label.

After base levels of thromboxane had been measured, the aspirin solution was first applied on the morning of Day 1 to the skin of the human subjects within an hour of mixing by rubbing the aspirin solution on the arms and/or chest of the subject. The application was repeated with freshly prepared solution for each of four additional mornings (Days 2–5) in the same manner. Between applications the subjects followed their normal schedule of bathing and showering. Eight hours after the fifth application (on Day 5) blood was drawn for salicylate levels and thromboxane levels to be determined. With one subject, blood was drawn for $TXA_2$ levels every day just before application of a new aspirin solution (i.e., approximately 24 hours after application of the previous aspirin solution). Hemoccults were also tested.

Two of the subjects continued daily application for another five days (total ten days). For Days 6 and 7, aspirin solutions freshly prepared as described above were used. Beginning with Day 8, a different aspirin preparation was used. This second preparation was prepared by crushing aspirin tablets containing approximately 975 mg aspirin to form a powder. The powder was then formed into a paste with approximately 2 ml of distilled water. This paste was then mixed with 4 ml propylene glycol and 4 ml ethanol to produce approximately 10 ml of a cloudy solution. This cloudy solution was then filtered to remove excipients and other insoluble material found in the crushed aspirin tablets. After filtering, approximately 10 ml of a clear solution was obtained which contained approximately 9% aspirin. 8 ml of the resulting solution was used in each application. This second solution was applied to the two continuing subjects as previously described. Salicylate and thromboxane levels were checked after the tenth day. Thromboxane levels are summarized in Table 1.

TABLE 1

| | Thromboxane Levels (ng/cc) | | | | | |
|---|---|---|---|---|---|---|
| Subject | Baseline | Day 2 | Day 3 | Day 4 | Day 5 | Day 10 |
| 1 | 401 | 311 | 250 | 199 | 105/35[1] | 18 |
| 2 | 372 | | | | 105 | 12 |
| 3 | 107[2] | | | | 124 | |
| 4 | 402 | | | | 152 | |
| 5 | 394 | | | | 25 | |

[1]The first number is the level measured in the morning of Day 5 prior to administration of the new Day 5 dose. The second number is the level measured eight hours after the Day 5 application
[2]Subject 3 had a very low measured baseline thromboxane level which is believed to have been a sampling error.

As summarized in the table, baseline thromboxane levels were found to range from 372–402 ng/cc in four out of five subjects. The low baseline for Subject 3 is believed to be erroneous and, as a result, the data for Subject 3 was not considered relevant. After five daily applications of aspirin in accordance with the present invention, caused a decrease in thromboxane levels of at least 50%. The two subjects that continued therapy in accordance with the present invention for another five days had marked suppression by Day 10 of 95 and 97% to levels of 18 and 12 ng/cc. Salicylate levels in four of five patients on day five were measured as 1 mg percent or less (approx. 1 mg percent being the lower limit of sensitivity of the assay.). All hemoccults taken were negative. No gastrointestinal symptoms or other side effects were noted or reported by the subjects.

EXAMPLE 2

Only healthy male and female volunteers were studied. The subjects were asked to avoid aspirin and any other cyclooxygenase inhibitors for the 10 days before and throughout the period of investigation. Aspirin (acetyl salicylic acid, USP) powder was dissolved in propylene glycol and either isopropyl alcohol or ethanol (1.7:1 v/v) to a final concentration of 94 mg/ml. Preliminary studies demonstrated that aspirin was stable in this vehicle, with less than 1% salicylate detected after 24 hr at room temperature. The aspirin preparation was made daily immediately prior to its application. Volunteers attended the clinic where the preparation was applied and were asked not to wash the area for at least 12 hours. The aspirin solution was applied to the forearm and upper arm over a 15 min interval. Volunteers received aspirin 250 mg (n=4), aspirin 750 mg (n=6) or vehicle (n=6) for 10 days and were followed for 8 days following drug withdrawal. The volunteers were aged 31–56 years, with equal numbers of male and females in each treatment group.

Blood without anticoagulant was obtained for serum $TXB_2$, the stable metabolite of $TXA_2$, prior to and at intervals during and following aspirin administration. The blood was allowed to clot in glass at 37° C. for 60 min and the serum removed and stored at −20° C. until analyzed. Urine was collected over 24 hours at corresponding times for measurement of 2,3-dinor-$TXB_2$ (TX-M) and 2,3-dinor-6-keto-$PGF_{1\alpha}$ (PGI-M), major enzymatic metabolites of $TXA_2$ and $PGI_2$, respectively [Lawson et al., Analyt. Biochem. 150:463 (1985); FitzGerald et al., N. Engl. J. Med. 310: 1065 (1984)]. Excretion of these products is an index of the in vivo formation of their parent compounds [FitzGerald et al., supra; Reilly and Fitzgerald, Blood 69: 180 (1987)]. Serum $TXB_2$ and urinary metabolites were determined by negative ion-chemical ionization, gas chromatography-mass spectrometry (NICI-GCMS) using authentic deuterated standards, as previously described [Braden et al., supra].

Figure 1:
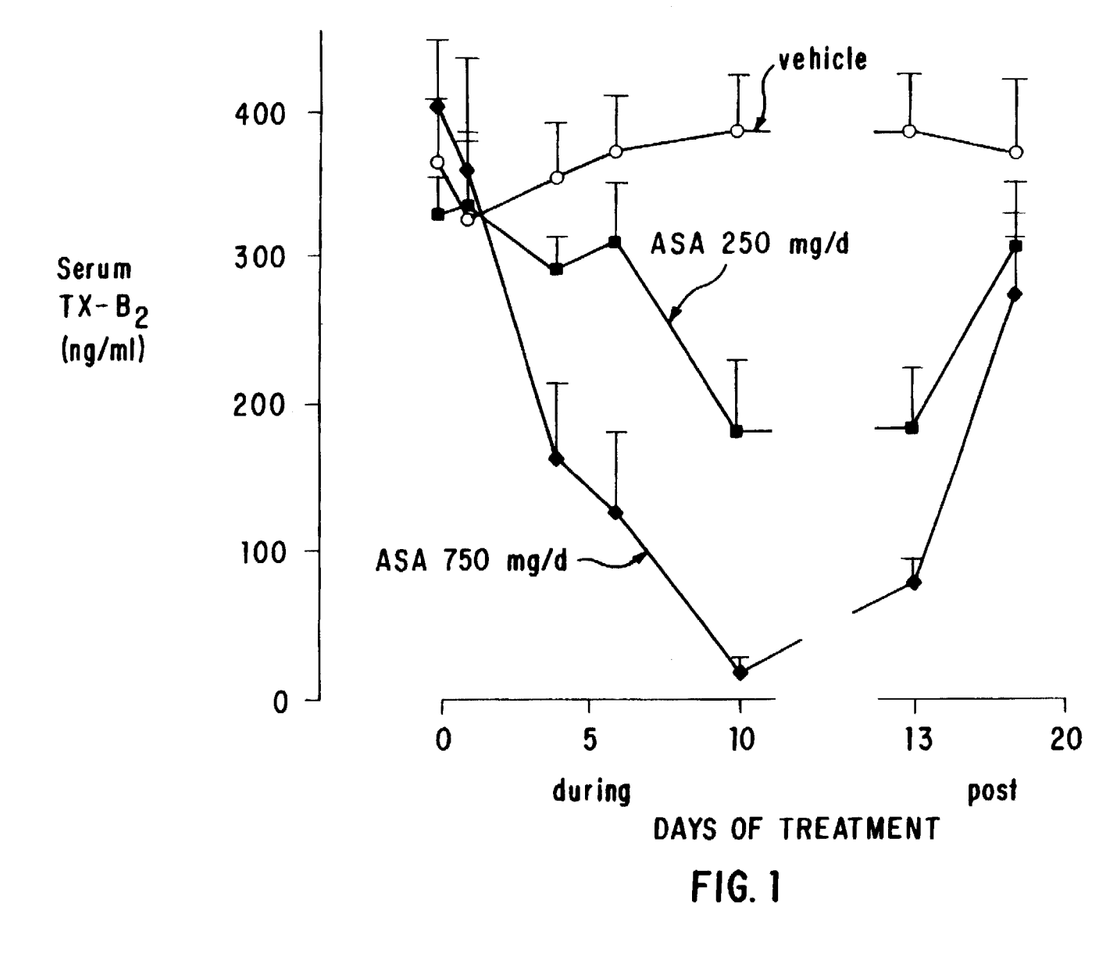
FIG. 1 is a graph of serum $TXB_2$ (ng/ml) levels during administration of dermal aspirin 250 mg/day and 750 mg/day vs. vehicle for 10 days and following withdrawal of therapy.

Serum $TXB_2$, an index of the capacity of platelets to generate $TXA_2$, was within the normal range in all subjects prior to study, demonstrating that none had been exposed to a cyclooxygenase inhibitor. Application of the vehicle alone had no effect on serum $TXB_2$ in 6 subjects (FIG. 1). With aspirin 750 mg/day (n=6), there was a progressive reduction in serum $TXB_2$ in all but one of the volunteers. In the remaining subjects, serum $TXB_2$ was 5±3% of baseline by day 10 of application (n=5, p=0.003; FIG. 1). Aspirin 250 mg/day induced a smaller fall in serum $TXB_2$, which was 55±11% by day 10 (n=4; p<0.01). Following the withdrawal of aspirin, serum $TXB_2$ increased gradually and by day 8 was 93±7 and 65±9% of baseline for aspirin 250 mg and 750 mg, respectively.

Figure 2:
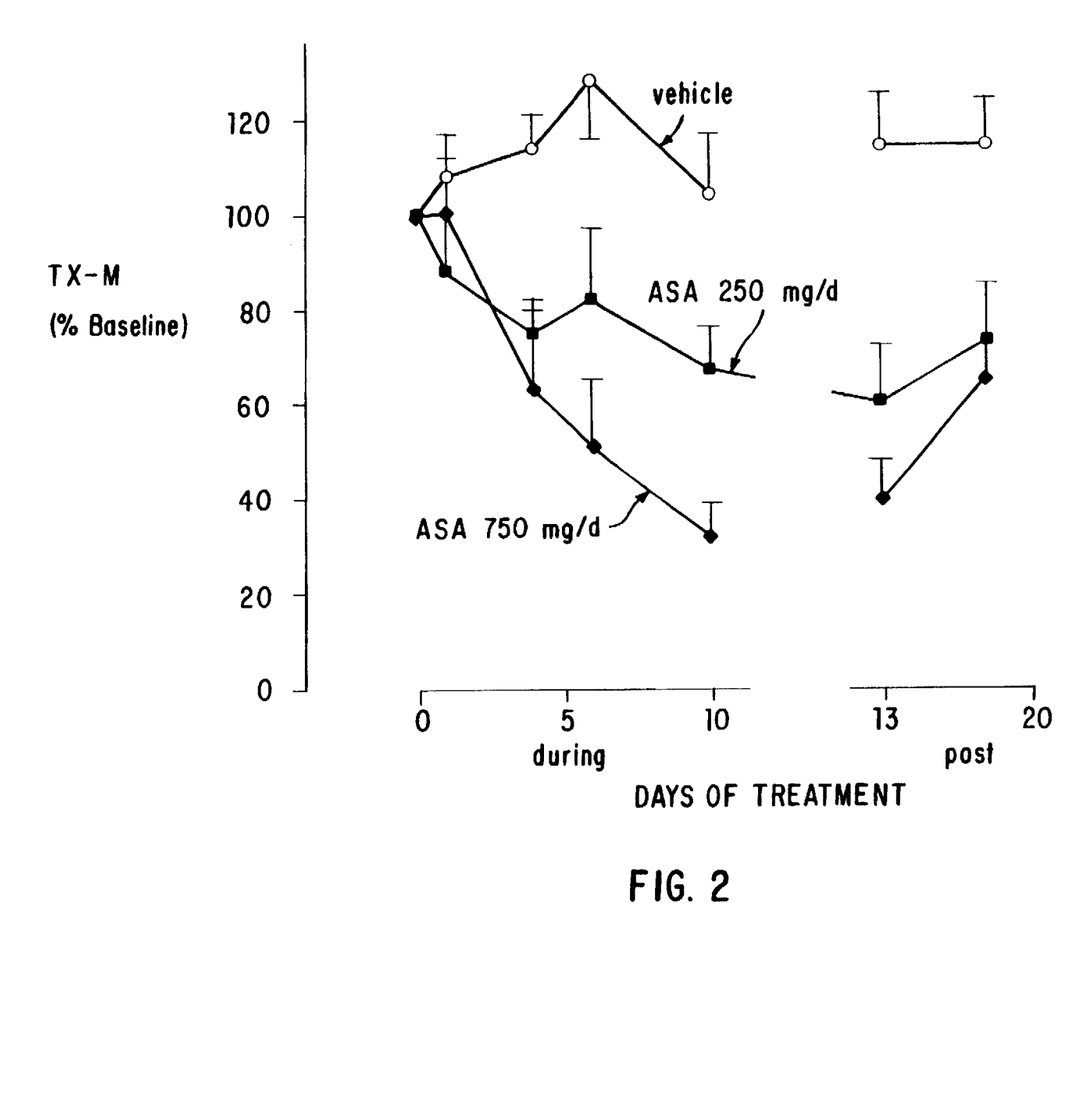
FIG. 2 is a graph of urinary excretion of 2,3-dinor $TXB_2$ (TX-M), expressed as a percent of baseline, during the administration of dermal aspirin or vehicle for 10 days and following withdrawal of therapy. Note that the baseline levels were 381±48, 440±56 and 498±76 pg/mg creatinine for vehicle, aspirin 250 mg and aspirin 750 mg groups, respectively.
Figure 3:
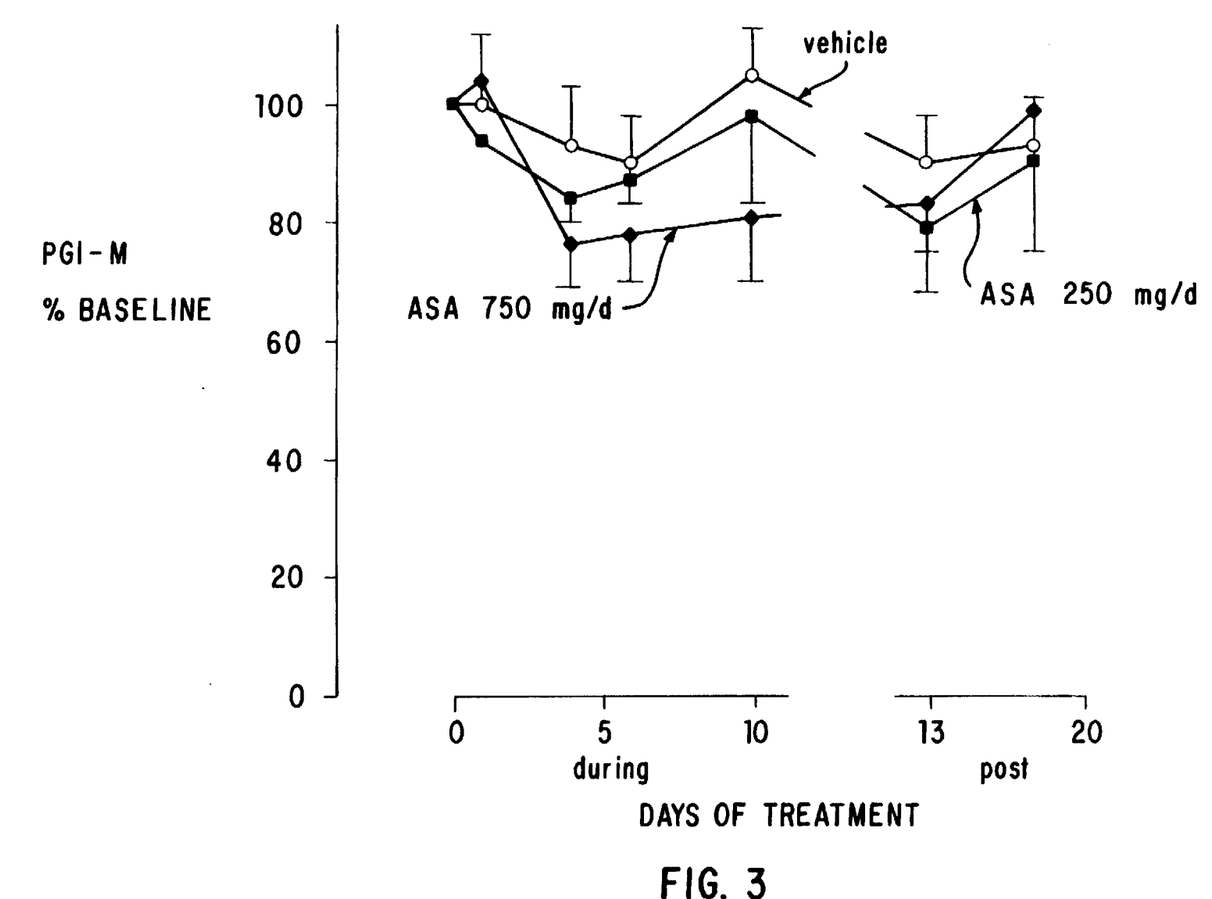
FIG. 3 is a graph of urinary excretion of 2,3-dinor-6-keto $PGF_{12}$ (PGI-M), expressed as a percent of baseline, during the administration of dermal aspirin or vehicle for 10 days and following withdrawal of therapy. Note that the baseline levels were 244±68, 402±139 and 248±73 pg/mg creatinine for vehicle, aspirin 250 mg and aspirin 750 mg groups, respectively.

$TXA_2$ biosynthesis demonstrated a similar response. Thus, there was a dose dependent reduction in the urinary excretion of TX-M. At 750 mg/day of dermal aspirin, TX-M declined gradually and was 32±7% of baseline by day 10 (n=5; p=0.002) of drug application. By 8 days following drug withdrawal, excretion of the metabolite had recovered to 65±9% of the pretreatment value (FIG. 2). Despite the evidence of marked inhibition of platelet cyclooxygenase, there was only a small fall in $PGI_2$ biosynthesis, based on urinary PGI-M determinations (FIG. 3). Although the changes did not achieve statistical significance (p=0.074 by ANOVA), there was an apparent dose response relationship. Thus, urinary excretion of PGI-M fell to 84±4% and 76±7% of baseline on aspirin 250 mg/day and 750 mg/day, respectively (FIG. 3). The peak decrease in PGI-M excretion occurred by day 4 on both doses, in contrast to TX-M excretion.

EXAMPLE 3

In an additional 4 subjects, we examined the increase in PGI2 formation in response to intravenous bradykinin prior to and following oral aspirin 75 mg or dermal aspirin 750 mg daily for 14 days. The protocol for bradykinin has been described previously [Clark, N. Engl. J. Med 325:1137 (1991)]. Volunteers were admitted after an overnight fast to the Clinical Research Center. Blood samples were obtained for serum $TXB_2$ and the subject asked to void. Through a peripheral vein, 1 liter of normal saline was infused over 1 hour. After a further hour, bradykinin was infused in incremental doses of 100–800 ng/kg/min, each over 15 min. The infusion was continued at the maximum tolerated dose for a total period of 2 hr. Blood pressure and heart rate were monitored continuously. Urine was collected in separate 2 hr aliquots prior to, during and following the bradykinin infusion.

Previous studies have demonstrated that bradykinin increases $PGI_2$ biosynthesis by on average 2–6 fold. In the 4 subjects studied, bradykinin induced a 5.1±6 fold increase in PGI-M excretion. Two subjects were treated with oral aspirin 75 mg/day for 14 days and two with dermal aspirin 750 mg/day. Both preparations caused a marked fall in urinary TX-M (TABLE 2). Oral aspirin resulted in a decrease in urinary PGI-M at rest and following stimulation with bradykinin. In contrast, resting and stimulated PGI-M excretion was largely unaltered by dermal aspirin.

TABLE 2[1]

|  |  | Dermal Aspirin (750 mg/day) | | Oral Aspirin (75 mg/day) | |
|---|---|---|---|---|---|
|  |  | PT 1 | PT 2 | PT 1 | PT 2 |
| TX-M | pre ASA | 220 | 121 | 136 | 111 |
|  | post ASA | 46 | 29 | 26 | 43 |
| PGI-M (rest) | pre ASA | 163 | 105 | 104 | 200 |
|  | post ASA | 138 | 149 | 63 | 96 |
| PGI-M (stim) | pre ASA | 1520 | 559 | 433 | 340 |
|  | post ASA | 1553 | 601 | 173 | 132 |

[1]The excretion of TX-M and PGI-M before and following dermal aspirin 750 mg/day or oral aspirin 75 mg/day for 10 days. Urine samples were collected over 2 hr before (rest) and following the administration of bradykinin (stim). Dermal aspirin suppressed TX-M, but not effect on PGI-M.

EXAMPLE 4

In 4 subjects (2 male, 2 female) demonstrating a marked (>90%) decrease in serum $TXB_2$, plasma aspirin and salicylate were determined at timed intervals (0, 0.25, 0.5, 0.75, 1, 1.5, 2, 4, 6, 8, 12 and 24 hr) following the application of aspirin on days 1 and 14. Aspirin was applied in a dose of 750 mg on one limb over a 15 min interval. Samples were drawn from the opposite arm. Blood was withdrawn into heparin (10 U/ml final concentration) and potassium fluoride (5% final concentration), the latter to prevent ex vivo metabolism of aspirin by plasma esterases. The plasma was separated immediately and stored at −700° C. until analyzed. Aspirin and its metabolite, salicylic acid, were measured by NICI-GCMS using deuterium-labelled analogues as internal standards, as previously described [Clark, supra].

Plasma aspirin and salicylate levels were determined following the single application of dermal aspirin in five subjects who demonstrated a marked (>90%) reduction in serum $TXB_2$. Plasma aspirin was barely detectable up to three hours following application when it rose to 237±114 ng/ml. At six hours, it fell to 52±14 ng/ml and by 24 hours it decreased to 4±3 ng/ml. Plasma salicylate demonstrated a similar pattern. At two hours, it was 69±20 ng/ml rising to 250±77 ng/ml at three hours. At six hours, plasma salicylate was 774±296 ng/ml. By twenty-four hours, the levels had fallen to 329±84 ng/ml. The later peak in salicylate levels is consistent with its being derived from aspirin. Moreover, this prolonged elevation of plasma salicylate is to be expected, given its longer plasma half-life. Note that levels following oral aspirin (75 mg) are 1–2 ug/ml.

Each of the references cited in this specification is incorporated herein by reference as if fully set forth.

What is claimed is:

1. A method for suppressing thromboxane levels in a mammalian subject that would benefit from suppression of such levels, said method comprising:
    contacting the skin of said subject with a pharmaceutical preparation comprising from about 250 mg to about 750 mg aspirin, said aspirin being percutaneously absorbed into said subject's bloodstream in an amount sufficient to reduce thromboxane levels in said subject by more than 50% without substantially affecting prostacyclin levels or resulting in gastrointestinal toxicity.

2. The method of claim 1 wherein, the pharmaceutical preparation contains 250 mg of aspirin.

3. The method of claim 1 wherein, the pharmaceutical preparation contains 750 mg of aspirin.

4. The method of claim 1, wherein said pharmaceutical preparation is in continuous contact with said skin for at least 4 successive days.

5. The method of claim 1, wherein said pharmaceutical preparation is in continuous contact with said skin for at least 10 successive days.

6. The method of claim 1, wherein said thromboxane levels are reduced to from less than 5% of baseline levels to less than 50% of baseline levels.

7. The method of claim 1, wherein said pharmaceutical preparation comprises about 9% aspirin.

* * * * *

UNITED STATES PATENT AND TRADEMARK OFFICE
CERTIFICATE OF CORRECTION

PATENT NO. : 5,763,425
DATED : June 9, 1998
INVENTOR(S) : Keimowitz et al.

It is certified that error appears in the above-identified patent and that said Letters Patent is hereby corrected as shown below:

Column 2, line 55, change "form" to -- form. --
Column 4, line 26, change "aspirin" to -- aspirin.--
Column 4, line 29, change "aspririn" to -- aspirin --
Column 5, line 8, delete "delaying a"
Column 5, line 13, change "systematically" to -- systemically --
Column 6, line 67, change "wa" to -- was --
Column 8, line 40, change "$PGF_{1a}$" to -- $PGF_{1a}$ --
Column 9, line 18, change "PGI2" to -- $PGI_2$ --
Column 9, line 61, change "but not effect on PGI-M" to -- but had no effect on PGI-M --
Column 10, line 13, change "-700°C" to -- -70°C --

Signed and Sealed this

Tenth Day of November 1998

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,763,425
DATED : June 9, 1998
INVENTOR(S) : Rudolph M. Keimowitz and Desmond J. Fitzgerald It is certified that error appears in the above-identified patent and that said Letters Patent is hereby corrected as shown below:

<u>Title page,</u>
Item [73], replace "Gundersen Clinic, Ltd., La Crosse, Wis." with
-- Gundersen Medical Foundation, Ltd., La Crosse, WI, and Vanderbilt University, Nashville, TN --

Signed and Sealed this

Fifth Day of November, 2002

*Attest:*

JAMES E. ROGAN
*Attesting Officer*     *Director of the United States Patent and Trademark Office*